(12) United States Patent
Kountotsis et al.

(10) Patent No.: US 8,844,337 B2
(45) Date of Patent: Sep. 30, 2014

(54) BREATH ACTUATION OF ELECTRONIC AND NON-ELECTRONIC DEVICES FOR PREVENTING UNAUTHORIZED ACCESS

(76) Inventors: Theodosios Kountotsis, East Elmhurst, NY (US); Agjah Libohova, E. Setauket, NY (US)

(*) Notice: Subject to any disclaimer, the term of this patent is extended or adjusted under 35 U.S.C. 154(b) by 220 days.

(21) Appl. No.: 13/066,969

(22) Filed: Apr. 29, 2011

(65) Prior Publication Data
US 2012/0272713 A1 Nov. 1, 2012

(51) Int. Cl.
*G01N 33/50* (2006.01)
*G01N 33/497* (2006.01)

(52) U.S. Cl.
CPC .................................. *G01N 33/497* (2013.01)
USPC ............................ 73/23.3; 73/23.2; 73/23.34

(58) Field of Classification Search
USPC ...................................... 73/23.2, 23.3, 23.34
See application file for complete search history.

(56) References Cited

U.S. PATENT DOCUMENTS

| | | | | |
|---|---|---|---|---|
| 5,048,321 | A * | 9/1991 | Chow | 73/23.3 |
| 5,361,758 | A * | 11/1994 | Hall et al. | 600/322 |
| 6,555,821 | B1 * | 4/2003 | Himberg et al. | 250/339.08 |
| 6,726,636 | B2 * | 4/2004 | Der Ghazarian et al. | 600/532 |
| 7,101,340 | B1 * | 9/2006 | Braun | 600/532 |
| 7,256,700 | B1 * | 8/2007 | Ruocco et al. | 340/576 |
| 7,287,617 | B2 * | 10/2007 | Mobley et al. | 180/272 |
| 7,352,465 | B2 * | 4/2008 | Fay et al. | 356/437 |
| 7,621,171 | B2 * | 11/2009 | O'Brien | 73/23.41 |
| 7,812,712 | B2 * | 10/2010 | White et al. | 340/426.2 |
| 7,820,108 | B2 * | 10/2010 | Lampotang et al. | 422/84 |
| 7,823,681 | B2 * | 11/2010 | Crespo et al. | 180/272 |
| 7,934,577 | B2 * | 5/2011 | Walter et al. | 180/272 |
| 7,972,277 | B2 * | 7/2011 | Oki et al. | 600/532 |
| 8,080,206 | B2 * | 12/2011 | Leddy et al. | 422/83 |
| 8,315,617 | B2 * | 11/2012 | Tadayon et al. | 455/418 |
| 2004/0081582 | A1 | 4/2004 | Brooke | |
| 2005/0053523 | A1 | 3/2005 | Brooke | |
| 2006/0193749 | A1 * | 8/2006 | Ghazarian et al. | 422/83 |
| 2007/0016092 | A1 | 1/2007 | Shaw et al. | |
| 2007/0167853 | A1 * | 7/2007 | Melker et al. | 600/532 |
| 2008/0077037 | A1 * | 3/2008 | Gouma et al. | 600/532 |
| 2010/0228141 | A1 | 9/2010 | Kountotsis | |
| 2010/0234064 | A1 | 9/2010 | Harris, Jr. | |
| 2012/0234708 | A1 * | 9/2012 | Chabot | 206/320 |

OTHER PUBLICATIONS

Keith Gavin, "New Cell Can Tell If You're Drunk", published on ABCNews.go.com on Jun. 27, 2006.*
"Breath Testing for Prosecutors Targeting Hardcore Impaired Drivers", American Prosecutors Research Institute, Dec. 2004.*

* cited by examiner

*Primary Examiner* — David A Rogers
(74) *Attorney, Agent, or Firm* — Theodosios Kountotsis

(57) ABSTRACT

An apparatus is presented including an input unit for receiving initial breath samples; a breath analysis module for analyzing the initial breath samples; a comparison module for comparing the initial breath samples to subsequent breath inputs; and a breath authorization module for locking and/or unlocking the apparatus in response to results received from the comparison module. The apparatus may also include a storage unit for storing the initial breath samples and the subsequent breath inputs. The breath analysis module is a chemical breath component analyzer configured to: (i) count each of a plurality of select volatile organic compounds from the initial breath samples and the subsequent breath inputs received from the input unit and (ii) determine a concentration of each of the plurality of the select volatile organic compounds.

20 Claims, 8 Drawing Sheets

BREATH ACTUATION OF ELECTRONIC AND NON-ELECTRONIC DEVICES FOR PREVENTING UNAUTHORIZED ACCESS

BACKGROUND

1. Field of the Related Art

The present disclosure relates to electronic and non-electronic devices, and more particularly, but not exclusively, to breath actuation of electronic and non-electronic devices for allowing authorized users access and preventing unauthorized use of such devices.

2. Description of the Related Art

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions. Therefore, unless otherwise indicated herein, what is described in this section is not prior art to the description and claims in this application and is not admitted to be prior art by inclusion in this section.

The tendency of users to store valuable information on their electronic devices is growing with the sophistication and diversification of electronic device usage and also with increased capacity of integrated storage media of electronic devices. With electronic devices used in offices or home environments or the like where they are easily usable by persons other than specific users who are authorized for their use, there is a risk that valuable information is revealed, lost or stolen. In order to prevent unauthorized access to electronic devices, it is well-known to register a password with the electronic device beforehand.

However, to prevent such an unauthorized access to an electronic device by means of a password, it is necessary not only to input a password every time the electronic device is powered on, but also to keep the registered password from being revealed to persons other than the specific user. As such, because the input, operation, and management of passwords are complicated, many users do not utilize the password function.

In addition, recently, it has been reported that about 70% of the crimes relating to the unauthorized access of electronic devices are committed by insiders. Therefore, even if passwords are used to secure the data or information, there is a possibility that a password may be known by the person attempting unauthorized access to the electronic device.

Therefore, it is an object of the present disclosure to provide, a system and method for preventing unauthorized access to electronic devices, as well as non-electronic devices. Additionally, it is clear that substantial room exists for affecting an advancement in the breath analysis art, which overcomes these shortcomings in a practical and efficient manner.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides for an electronic device including a processing unit for executing a plurality of operations; an input module for receiving breath samples; a breath analysis module for analyzing the breath samples; and a breath authorization module for allowing and/or preventing access to the plurality of operations of the electronic device in response to results received from the breath analysis module.

The electronic device may further include a storage unit for storing the plurality of operations and the breath samples.

In another exemplary embodiment, the breath analysis module includes one or more sensors for sensing at least molecules and volatile organic compounds collected from the breath samples received from the input module. The breath analysis module also includes a comparison unit for comparing initial breath samples received for initialization with subsequent breath samples received for access.

The electronic device is at least one of a mobile device, a cell phone, a smart phone, a personal computing device, an electronic book, an electronic tablet, a digital camera, a printing device, a multi-functional printing device, a camcorder, a television, a gaming system, an MP3 device, a security device, a tracking device, a fingerprint device, an Internet device, and automotive components.

In another exemplary embodiment, the electronic device is one of a portable device and a non-portable device. The input module is at least one of an orifice, an inlet, and an opening.

In yet another exemplary embodiment, the electronic device may further include an output indication unit for indicating whether the breath samples received from the input module allow access or prevent access to the plurality of operations, the output indication unit being one of a visual indication or an audible indication or a combination thereof.

In yet another exemplary embodiment, the electronic device may further include an override function for overriding the breath authorization module.

In yet another exemplary embodiment, a first breath input permits access to a first set of operations and a second breath input permits access to a second set of operations, the second set of operations being different than the first set of operations.

The present disclosure provides for an apparatus including an input unit for receiving initial breath samples; a breath analysis module for analyzing the initial breath samples; a comparison module for comparing the initial breath samples to subsequent breath inputs; and a breath authorization module for locking and/or unlocking the apparatus in response to results received from the comparison module.

The breath analysis module may be a chemical breath component analyzer configured to: (i) count each of a plurality of select volatile organic compounds from the initial breath samples and the subsequent breath inputs received from the input unit and (ii) determine a concentration of each of the plurality of the select volatile organic compounds.

The comparison module compares a plurality of select volatile organic compounds and a concentration of each of the plurality of select volatile organic compounds detected in the subsequent breath inputs with predetermined volatile organic compounds and predetermined ranges of concentration of select volatile organic compounds.

The apparatus is at least one of an electronic device, a door, a safe, an appliance, a utensil, a machine, a tool, an instrument, a gadget, a mechanical mechanism, an electrical mechanism, and an electro-mechanical mechanism.

The present disclosure also provides a method of accessing an apparatus, including receiving initial breath samples from an input unit; analyzing the initial breath samples via a breath analysis module; comparing the initial breath samples to subsequent breath inputs via a comparison module; storing the initial breath samples and the subsequent breath inputs via a storage unit; and locking and/or unlocking the apparatus in response to results received from the comparison module via a breath authorization module.

The present disclosure also provides a method for manufacturing an electronic device including forming/constructing/fabricating a processing unit for executing a plurality of operations; forming/constructing/fabricating an input module for receiving breath samples; forming/constructing/fabricating a breath analysis module for analyzing the breath samples; and forming/constructing/fabricating a breath authorization module for allowing and/or preventing access to the plurality of operations of the electronic device in response to results received from the breath analysis module.

The present disclosure also provides a method for manufacturing an apparatus including forming/constructing/fabricating an input unit for receiving initial breath samples; forming/constructing/fabricating a breath analysis module for analyzing the initial breath samples; forming/constructing/fabricating a comparison module for comparing the initial breath samples to subsequent breath inputs; and forming/constructing/fabricating a breath authorization module for locking and/or unlocking the apparatus in response to results received from the comparison module.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the present disclosure will be described herein below with reference to the figures wherein.

Figure 1:
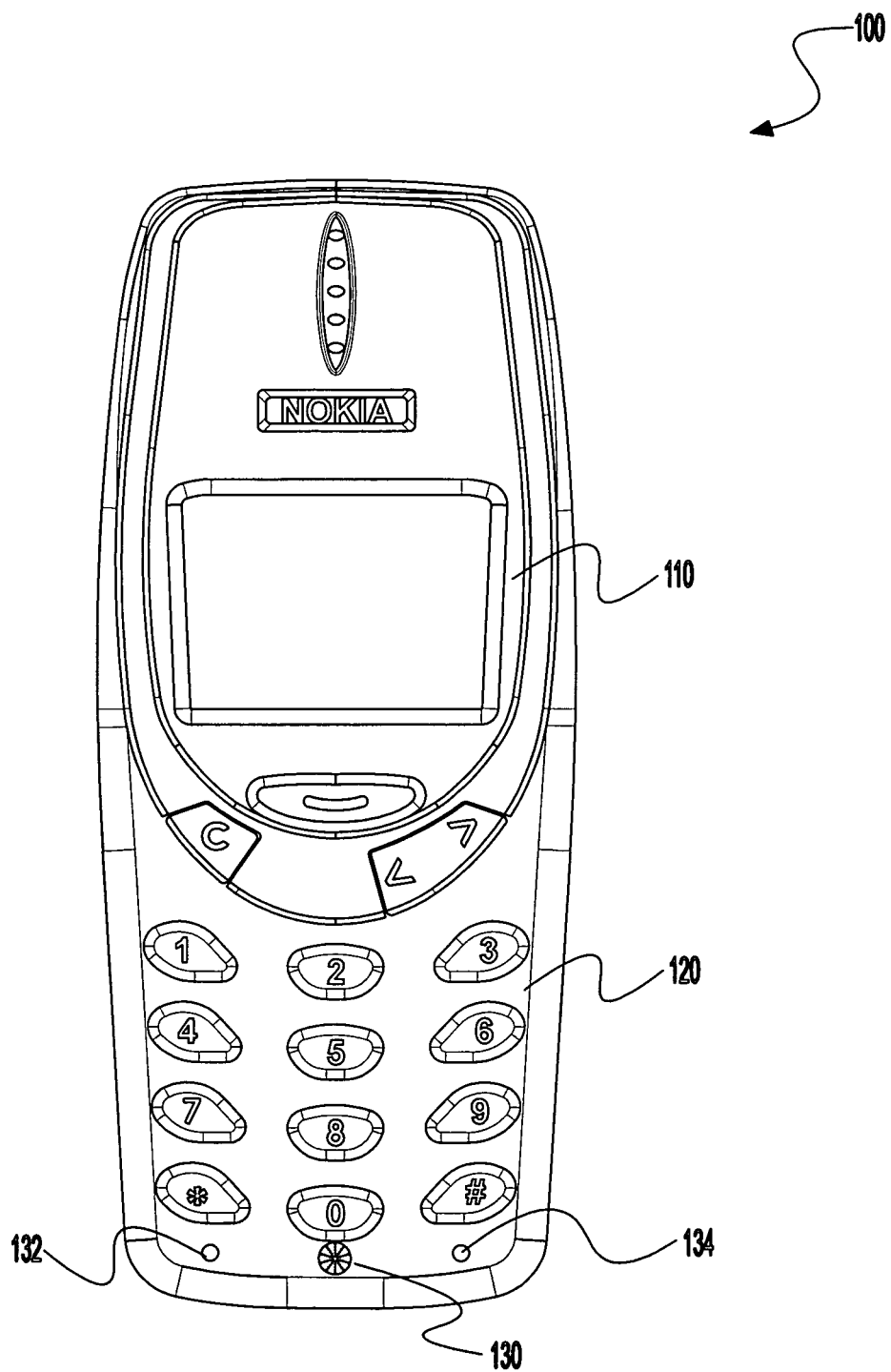
FIG. 1 is a perspective view of a mobile device including a breath analysis module and a breath authorization module for allowing and/or preventing access to the plurality of operations of the mobile device, in accordance with the present disclosure.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Accordingly, while the present disclosure is susceptible to various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is intended to cover all modifications, equivalents, and alternatives falling within the spirit and scope of the present disclosure as defined by the claims. Like numbers refer to like elements throughout the description of the figures.

Unless otherwise indicated, all numbers expressing quantities and conditions, and so forth used in the specification and claims are to be understood as being modified in all instances by the term "about." The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

The present disclosure is described below with reference to block diagrams and/or flowchart illustrations of methods, apparatus (systems and/or devices) and/or computer program products according to embodiments of the present disclosure. It is understood that a block of the block diagrams and/or flowchart illustrations, and combinations of blocks in the block diagrams and/or flowchart illustrations, may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

Prior to describing the present disclosure in further detail, it will first be helpful to define various terms that will be used throughout the following discussion. For example:

The term "electronic device" may refer at least to one or more personal computers (PCs), a standalone printer, a standalone scanner, a mobile phone, an MP3 player, audio electronics, video electronics, GPS systems, televisions, recording and/or reproducing media (such as CDs, DVDs, camcorders, cameras, etc.) or any other type of consumer or non-consumer analog and/or digital electronics. Such consumer and/or non-consumer electronics may apply at least in any type of entertainment, communications, home, and/or office capacity. Thus, the term "electronic device" may refer to any type of electronics suitable for use with a circuit board and intended to be used by a plurality of individuals for a variety of purposes. The electronic device may be any type of computing and/or processing device.

Additionally, "electronic devices" may refer to at least, or may include but are not limited to, a mouse, keyboard, Bluetooth™ adapter, global positioning system (GPS) receiver, remote control, audio module, user interface module, electronic-book reader module, radio frequency identification (RFID) reader, barcode reader, digital projector, universal serial bus stick, magnetometer, fingerprint reader, current/voltage measuring device, electrocardiogram, pulse measuring device, and stethoscope. Additionally, "electronic devices" may refer to at least, or may include but are not limited to, an electronic book, displays, television sets, electronic paper, watches, electronic calculators, cellular phones, personal digital assistants, cellular telephone, view finder, direct view type video tape recorder, car navigation system, pager, electronic notebook or personal computer (PC), electric calculator, word processor, work station, picture telephone, point of sale (POS) terminal(s), point-of-entry (POE) terminal(s) and any type of electrical or mechanical or electromechanical apparatus/system/configuration with one or more touch panels.

The term "processing" or "processor" may at least refer to determining the elements or essential features or functions or processes of one or more breath recognition, collection, and analysis systems for computational processing. The term "process" or "processor" may further refer to or encompass or include tracking data and/or collecting data and/or manipulating data and/or examining data and/or updating data on a real-time basis in an automatic manner and/or a selective manner and/or manual manner (continuously or periodically or intermittently).

The term "apparatus" may refer to at least a device, a system, an appliance, a contraption, a machine, a mechanism, utensils, tools, implements, instruments, gadgets, and widgets. The term "apparatus" may be used interchangeably with the term "electronic device."

The term "module" may refer to at least a self-contained component (unit or item) that is used in combination with other components and/or a separate and distinct unit of hardware or software that may be used as a component in a system, such as a breath analyzing system. The term "module" may also refer to at least a self-contained assembly of electronic components and circuitry, such as a stage in a computer that is installed as a unit. The term "module" may be used interchangeably with the term "unit."

The term "analyze" may refer to at least determining the elements or essential features or functions or processes of a plurality of analyzing modules in a breath analysis assembly and/or to subject the plurality of analyzing modules in a breath analysis assembly to computational processing. The term "analyze" may further refer to at least tracking data and/or collecting data and/or manipulating data and/or examining data and/or updating data and/or inspecting data and/or distinguishing data on a real-time basis in an automatic manner and/or a selective manner and/or manual manner (continuously, repeatedly, and/or intermittedly).

The term "storage unit" may refer to data storage. "Data storage" may refer to at least any article or material (e.g., a hard disk) from which information is capable of being reproduced, with or without the aid of any other article or device. "Data storage" may also refer to at least the holding of data in an electromagnetic form for access by a computer processor. Primary storage is data in random access memory (RAM) and other "built-in" devices. Secondary storage is data on hard disk, tapes, and other external devices. "Data storage" may also refer to at least the permanent holding place for digital data, until purposely erased. "Storage" implies a repository that retains its content without power. "Storage" mostly means magnetic disks, magnetic tapes and optical discs (CD, DVD, etc.). "Storage" may also refer to non-volatile memory chips such as flash, Read-Only memory (ROM) and/or Electrically Erasable Programmable Read-Only Memory (EEPROM).

The term "computing subsystem" may refer to at least any type of programmable machine, such as a computer, where the programmable machine may execute a programmed list of instructions and respond to new instructions that it is given. The term "computing subsystem" may also refer to a machine for performing calculations automatically or to a machine that manipulates data according to a list of instructions or to a programmable device that performs mathematical calculations and logical operations, especially one that may process, store and retrieve large amounts of data very quickly. The term "computing subsystem" may also refer to any type of device that stores and processes information, where the information is stored internally or externally either temporarily or permanently. The term "computing subsystem" may be used interchangeably with the term "processor."

The word "exemplary" is used herein to mean "serving as an example, instance, or illustration." Any embodiment described herein as "exemplary" is not necessarily to be construed as preferred or advantageous over other embodiments.

To this point, in conventional systems, breath analysis has been used solely for the detection of diseases and to methods of detecting, collecting, and inspecting breath samples for specific trace compounds. However, breath analysis has not been used for detecting molecules and/or organic compounds in order to access or prevent access to/from electronic devices and/or non-electronic devices.

Consequently, there is no system or method for using breath analysis to allow or prevent (authorize, enable, actuate, approve, confirm) access to an electronic/non-electronic device by using breath as an authorization variable (breath actuated prevention/authorization system). In particular, presently, there are no breath analysis systems or methods that prevent unauthorized users from accessing electronic devices, such as, for example, at least televisions, personal computers, MP3 players, cell phones, smart phones, iPhones®, telecommunications devices, and non-electronic devices, such as, for example, at least doors, safes, and/or power tools. Also, what is desired is an optimized sample collection system with superior detection capabilities where the sample collection system and the detection system are small in size, ideally hand-held or portable, without compromising sensitivity and selectivity of the compound of interest for detection.

Researchers have shown that the chemical composition of expired breath may be an accurate, timely, and painless indicator of the health of an individual. For example, researchers have used light absorption and emission by molecules as a means for qualitatively identifying which molecules are present in a mixture, and quantitatively determining what concentration of each is present. Commonly, molecules with two or more atoms show distinct absorptions in the infrared region of the spectrum. The detailed characteristics of these absorptions may be extremely sharp at low pressure for molecules that are in the gas phase, enabling the accurate determination of organic compounds/molecules present in breath. However, as previously mentioned, breath analysis has been very limited to only diagnosing diseases by detecting molecules in alveolar breath only (further described below). Consequently, there is no system or method for using breath analysis to allow/permit or prevent access from unauthorized use of electronic and non-electronic devices.

The present disclosure refers to a system and method that enables or authorizes or confirms or qualifies a user in order to prevent unauthorized access of electronic and non-electronic devices via breath analysis capabilities.

The present disclosure teaches a chemical analysis method related to human breath. The present disclosure further teaches a method of collecting human breath samples, analyzing such human breath samples, storing such human breath samples, and utilizing such human breath samples to allow or prevent access to electronic and non-electronic devices. The breath profile/breath concentration profile that is created may include a number of different molecules and/or organic compounds detected in human breath (either dead air space breath or alveolar breath or a combination thereof). For instance, human (and animal) breath contains hundreds of different trace volatile organic compounds (VOCs), in addition to the usual large amounts of $H_2O$ and $CO_2$. Thus, these types of VOCs would be valuable in creating a unique breath profile for a user and using that unique profile to allow and/or prevent access to electronic and non-electronic devices.

Moreover, as mentioned above, there are two types of breath, that is, dead air space breath and alveolar breath. Dead air space breath is exhaled breath, whereas alveolar breath is breath located in the lungs. Dead air space breath may include hundreds, if not thousands, of different molecules/organic compounds. Also, alveolar breath, may include hundreds, if not thousands, of different molecules/organic compounds.

However, few molecules/organic compounds in each type of breath are common to all individuals. In fact, the majority of molecules/organic compounds in each type of breath is unique and is contained in varying numbers and concentrations per individual. As a result, breath may provide a unique snapshot/fingerprint/blueprint/signature of an individual, thus identifying/distinguishing such individual, as does DNA (Deoxyribonucleic acid), for example. In particular, the main role of DNA molecules is the long-term storage of information. Similarly to DNA, breath stores/includes/encompasses information regarding an individual that is unique to that individual. By selectively counting unique molecules and/or organic compounds, and identifying such molecules and/or organic compounds, and measuring the concentration of each molecule and/or organic compound, a unique breath profile may be created that uniquely identifies or classifies or distinguishes or establishes or singles out a person and/or is used to allow or prevent access to electronic and non-electronic devices.

As a result, in the exemplary embodiments of the present disclosure, breath is used as a blueprint or fingerprint or signature to identify/distinguish the unique breath of the user. The rich assortment of chemical substances present in an individual's breath may reveal a great deal about the person doing the breathing, including providing a unique snapshot or blueprint or signature of the organic compounds/molecules (number and concentration) exuded from one's breath to allow or prevent access to electronic and non-electronic devices.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

With reference to FIG. 1, there is presented a perspective view of a mobile device including a breath analysis module and a breath authorization module for allowing and/or preventing access to the plurality of operations of the mobile device, in accordance with the present disclosure.

The mobile device 100 includes a user interface 110, input keys 120, and a breath receiving unit 130. Additionally, the mobile device 100 may include a first indication mechanism 132 and a second indication mechanism 134. The mobile device 100 may be a cell phone or a smart phone or an iPhone® or any other portable telecommunications device for receiving and transmitting signals.

In operation, the detecting and collecting of organic compounds/molecules in a breath sample may include a user breathing or exhaling into the breath receiving unit 130 of the mobile device 100 to absorb at least one breath molecule/organic compound. The breath is collected in an exhaled breath collector located in the breath analysis module 230 (see FIGS. 2A and 2B). The breath analysis module 230 analyzes the breath sample and extracts one or more molecules and/or organic compounds. This data may be stored in a storage unit 236, as discussed below with reference to FIG. 2B, such as a memory, as defined herein. The results of the breath analysis module 230 may be used to trigger the first and second indication mechanisms 132, 134.

For example, if a user is permitted to access the mobile device 100, the first indication mechanism 132 may be an LED that turns green, whereas if the user is not permitted to access the mobile device 100, the second indication mechanism 134 may be an LED that turns red. One skilled in the art may contemplate using a plurality of different indication and/or notification mechanisms for indicating whether the user is permitted or not permitted to access the mobile device 100. The plurality of indication mechanisms may be visual mechanisms or audible mechanisms or a combination thereof. For example, the words, "access permitted" and "access denied" may be displayed on the user interface 110 to indicate the result or the words "open" and "closed" may be displayed on the user interface 110 to indicate the result. However, any type of message conveying any type of information may be indicated on the on the user interface 110 or via the first and second indication mechanisms 132, 134. Also, the first and second indication mechanisms 132, 134 may be of any size imaginable, from a few millimeters to a few inches and constructed from any type of materials (LEDs, LCDs, or flexible displays). In addition, the first and second indication mechanisms 132, 134 may be optional.

Therefore, in operation, a breath of a user is sampled and collected. The breath may be analyzed for a specified or pre-defined or predetermined number of VOCs by the breath analysis module 230 (see FIGS. 2A and 2B). The VOCs are analyzed to determine if there is a match with an initial set of VOCs collected during initialization of the breath analysis module 230. The breath analysis module 230 may include a database of VOCs that that are compared to collected VOCs to indicate the breath characteristics of the user.

For example, it is preferable that uncommon molecules and/or organic compounds be selected for comparison. There may be hundreds or even thousands of molecules and/or organic compounds from which to select a number of desirable combinations for comparison purposes. For example, 100 uncommon organic compounds may be selected to form a unique breath profile for a person. However, 200, 300 or even 400 uncommon organic compounds may be selected to form a unique breath profile for a person. In addition, 200 unique molecules and 200 unique organic compounds may be selected to form a unique breath profile for a person.

In other words, any uncommon/common organic compounds may be selected, any uncommon/common molecules may be selected, or any combination of molecules and organic compounds may be selected to form any type of desirable unique breath profile (number of items and concentration of items may be examined). Of course, any type of variables may be measured and/or identified and/or collected that would be satisfactory for creating any type of unique breath profile pertaining to a person. One skilled in the art could envision using any chemical analysis techniques and using any chemical variables with any type of chemical characteristics to obtain a preferred unique breath profile for allowing or preventing access to the mobile device 100 or any other type of electronic device, as defined herein.

Figures 2A, 2B:
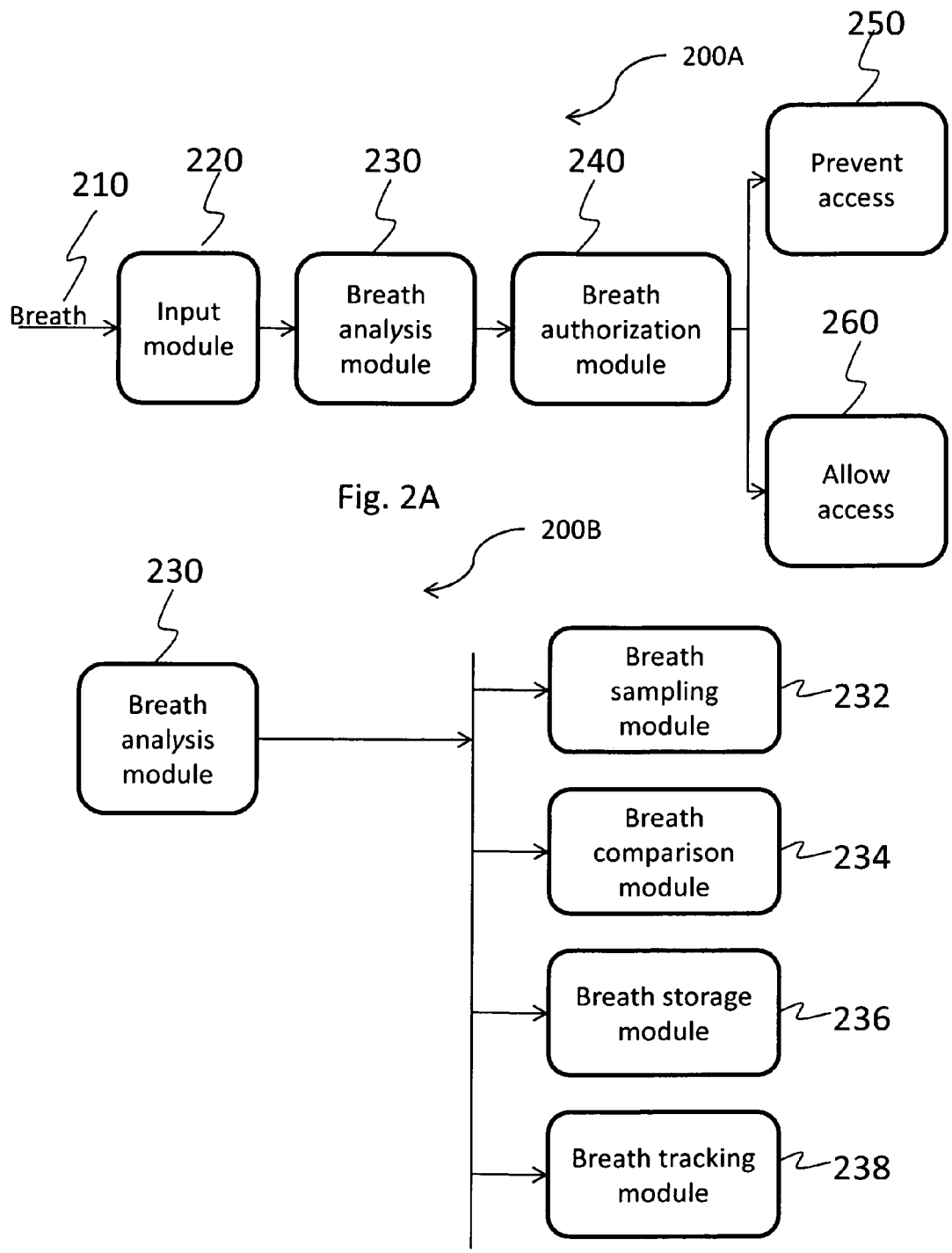
FIG. 2A is a block diagram illustrating a flow sequence of analyzing breath via the mobile device of FIG. 1, in accordance with the present disclosure.
FIG. 2B is a block diagram illustrating the components of the breath analysis module shown in FIG. 2A, in accordance with the present disclosure.

Therefore, a user may provide initial breath samples to the mobile device 100 for initializing the breath analysis module 230 (see FIGS. 2A and 2B). In other words, the breath analysis module 230, based on breath samples provided, creates an initial breath profile of the user and stores it either locally on the storage unit 236 of the mobile device 100 or remotely in an external database. The initial breath profile may be created based on a number of different molecules and/or VOCs collected from the breath of the user. Subsequently, when the user wishes to access the mobile device 100, the user may be prompted to input a breath sample via the breath receiving unit 130. The subsequent breath samples collected may be compared to the initial breath profile to determine if a match has occurred. If a match has occurred, the user is permitted to access the mobile device 100. If a match has not occurred, it is determined that an unauthorized user is attempting to access the mobile device 100 and access is denied. Therefore, access to the mobile device 100 is only permitted by verifying that subsequent received breaths match the initial breath profile. This process will be further described with reference to FIGS. 3 and 4.

Therefore, in summary, the breath analysis module 230 may be a chemical breath component analyzer configured to: (i) count each of a plurality of select volatile organic compounds from the initial breath samples and the subsequent breath inputs received from the input unit and (ii) determine a concentration of each of the plurality of the select volatile organic compounds. Additionally, a comparison module compares a plurality of select volatile organic compounds and a concentration of each of the plurality of select volatile organic compounds detected in the subsequent breath inputs with predetermined volatile organic compounds and predetermined ranges of concentration of select volatile organic compounds, as will be described below with reference to FIG. 2B.

With reference to FIG. 2A, there is presented a block diagram illustrating a flow sequence of analyzing breath via the mobile device of FIG. 1, in accordance with the present disclosure. With reference to FIG. 2B, there is presented a block diagram illustrating the components of the breath analysis module shown in FIG. 2A, in accordance with the present disclosure.

The block diagram 200A depicts breath 210 as an input to the input module 220. The breath 210 is analyzed via the breath analysis module 230. The analyzed breath may then be provided to the breath authorization module 240. The breath authorization module 240, based on the breath 210 received, either prevents access 250 or allows access 260 to an electronic device, as defined herein.

The block diagram 200B depicts the components of the breath analysis module 230. The breath analysis module 230 may include a breath sampling module 232, a breath comparison module 234, a breath storage module 236, and a breath tracking module 238.

The breath analysis module 230 analyzes the one or more samples of breath provided by the breath sampling module 232 (see FIG. 2B). The breath analysis may be executed by using any type of breath analysis techniques, such as spectroscopy/spectrometry and/or gas chromatography. One skilled in the art may envision any type of suitable breath analysis techniques.

For example, spectroscopy pertains to the dispersion of an object's light into its component colors (i.e., energies). By performing this dissection and analysis of an object's light, researchers may infer the physical properties of that object (such as temperature, mass, luminosity, number of molecules, number of organic compounds, and composition or concentration of molecules/organic compounds). Spectrometry is the spectroscopic technique used to assess the concentration or amount of a given species. In those cases, the instrument that performs such measurements is a spectrometer or spectrograph. Spectroscopy and/or spectrometry is often used in physical and analytical chemistry for the identification of substances through the spectrum emitted from or absorbed by them. Mass spectroscopy is a detection method, which may be coupled with chromatography or sample directly from the headspace of a sample, which ionizes, fragments, and rearranges a molecule under a given set of conditions and makes identification of the molecular weight/charge (m/z) of molecules possible.

However, any type of spectrometry and/or spectroscopy may be used, such as, but not limited to, electromagnetic spectroscopy, electron spectroscopy, mass spectroscopy, absoprtion spcetroscopy, emission spectroscopy, infrared spectroscopy, ultraviolet spectroscopy, thermal spectroscopy, laser spectroscopy, and/or scattering spectroscopy. One skilled in the art may envision any type of spectroscopy and/or spectrometry techiniques used to analyze breath from breath samples.

Chromatography pertains to a broad range of physical methods used to separate and or to analyze complex mixtures. The components to be separated are distributed between two phases: a stationary phase bed and a mobile phase which percolates through the stationary bed. Chromatography is a collective term for a family of laboratory techniques for the separation of mixtures. It involves passing a mixture dissolved in a "mobile phase" through a stationary phase, which separates the analyte to be measured from other molecules in the mixture and allows it to be isolated. Chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector, such as a Flame Ionization Detector (FID) or an Electrochemical Detector (ECD), converts the column eluent to an electrical signal that is measured and recorded.

However, any type of chromatography may be used, including, but not limited to, gas chromatography, affinity chromatography, and/or ion exchange chromatography. One skilled in the art may envision any type of chromatography techiniques used to analyze breath from breath samples.

Therefore, the present disclosure is not limited to only these two types of breath analysis techniques. Any type of breath analysis technique or combination thereof may be used to analyze breath samples from humans, animals, and/or plants.

In the exemplary embodiments of the present disclosure, breath analysis may refer to extracting a number of molecules and/or a number of organic compounds and/or a concentration for each of the molecules and/or organic compounds. The breath analysis module 230 may be pre-programmed to selectively choose which of the plurality of molecules and/or organic compounds to use for creating a unique breath profile. The breath analysis module 230 may choose select uncommon molecules and/or uncommon organic compounds to create a unique breath profile. The breath analysis module 230 may identify the concentration of each select uncommon molecule and/or organic compound. The unique breath profile may be created by using a plurality of different variables contained in breath that would be deemed satisfactory to provide for a unique breath profile. The exemplary embodiments are not limited to any specific variables or to any specific concentration of variables. All these variables may be predetermined/preset (factory settings/default settings) or may be uniquely prepared/modified based on the user.

Moreover, regarding the breath analysis module 230, a plurality of sensors may be included therein. The sensors may be any type of oxygen sensors or chemical sensors. In addition, several vapor sensing technologies, including conducting polymers, electrochemical cells, infrared spectroscopy, ion mobility spectrometry, metal oxide semiconductor, photo-ionized detectors, Fourier transforms, non-dispersive infrared spectrometry, elected ion flow tubes, and surface acoustic wave sensors, have been evaluated for detection of compounds in breath. Sensor sensitivity, selectivity, operating life, shelf-life, drift, linearity, initial cost, recurring costs, warm-up time, analysis time, power consumption, portability and calibration needs may also be evaluated to decide on the desired technique.

Additionally, the breath analysis module 230 may use/manipulate any type of electronic means/electronic devices to analyze the breath sample provided by the breath sampling module 232. For example, any type of microprocessor or processor or computing subsystem, as defined herein, may be used to execute such operations.

Referring to FIG. 2B, the breath sampling module 232 receives one or more breaths 210 and takes one or more samples from those breaths 210. The samples may be a section, a fragment, an instance, a part, a pattern, a piece, a portion, a segment or a unit of breath 210. Several samples may be extracted for accuracy and a portion of each sample may be used or a portion of select samples may be used. In other words, the breath sampling module 232 may receive several input breaths 210 and selectively decide which breaths 210 to accept. The breath sampling module 232 may accept one sample from one breath or a plurality of samples from several breath inputs from the same user. One skilled in the art may contemplate using a plurality of different scenarios or configurations in order to manipulate the most appropriate breath samples.

As discussed above with reference to FIG. 1, and referring to the breath comparison module 234, the breath analysis module 230 may further determine whether there is a match between a unique breath sample saved in the memory device (e.g., storage unit or breath storage module 236) and subsequent breaths received via the input module 220. In other words, several breaths from several different users may be entered via the same input module 220 and a determination may be made whether any of those subsequent breath samples matches the first or initial breath sample (or breath profile) in order to determine is access should be permitted or denied. Therefore, the breath comparison module 234 may compare the initial breath sample(s) stored in the breath storage module 236 with subsequent breaths received in order to determine if a match has occurred in order allow or prevent access to the electronic devices, as defined herein.

A match may occur in a variety of ways. For example, a plurality of molecules may be collected or a plurality of organic compounds may be collected or a combination of a plurality of molecules and organic compounds may be collected. This plurality of molecules and/or organic compounds may be extracted from dead air space breath, from alveolar breath or a combination of dead air space breath and alveolar breath. The match may require any number and concentration of matching molecules and/or organic compounds.

Referring back to FIG. 2A, an authorization module 240 may determine whether there is a match between a unique breath sample (or breath profile) saved in the memory device and subsequent breaths received via the input module 220. In other words, several breaths from several different individuals may be entered via the input module 220 and a determination needs to be made whether any of those subsequent breath samples matches the first breath sample (during initialization) in order to permit access to the contents of the electronic devices, as defined herein. The authorization module 240 optionally communicates with the first and second indications mechanisms 132, 134 or user interface 110 (see FIG. 1) to provide for a means of informing the user whether access has been permitted 260 or denied 250.

Referring back to FIG. 2B, the tracking module 238 may record and track the breath input activity. In other words, each time a breath sample is entered via the input module 220 of the electronic device, an instance of such input may be recorded and saved in the memory device or storage unit 236, as defined herein. Such information may be transmitted (wired or wirelessly) to a computing subsystem (such as a personal computer (PC) or other mobile devices, such as a cell phone or any other electronic device, as defined herein), where the authorized user may track the historical data related to breath samples inputted over a period of time. Additionally, the original breath profile of the authorized user may be monitored for slight deviations and the electronic processing means may decide to provide slight/minor updates to the existing original breath profile based on any deviations experienced. This may be executed in an automatic manner by an electronic processing means (e.g., a processor) located in the breath analysis module 230.

Figure 3:
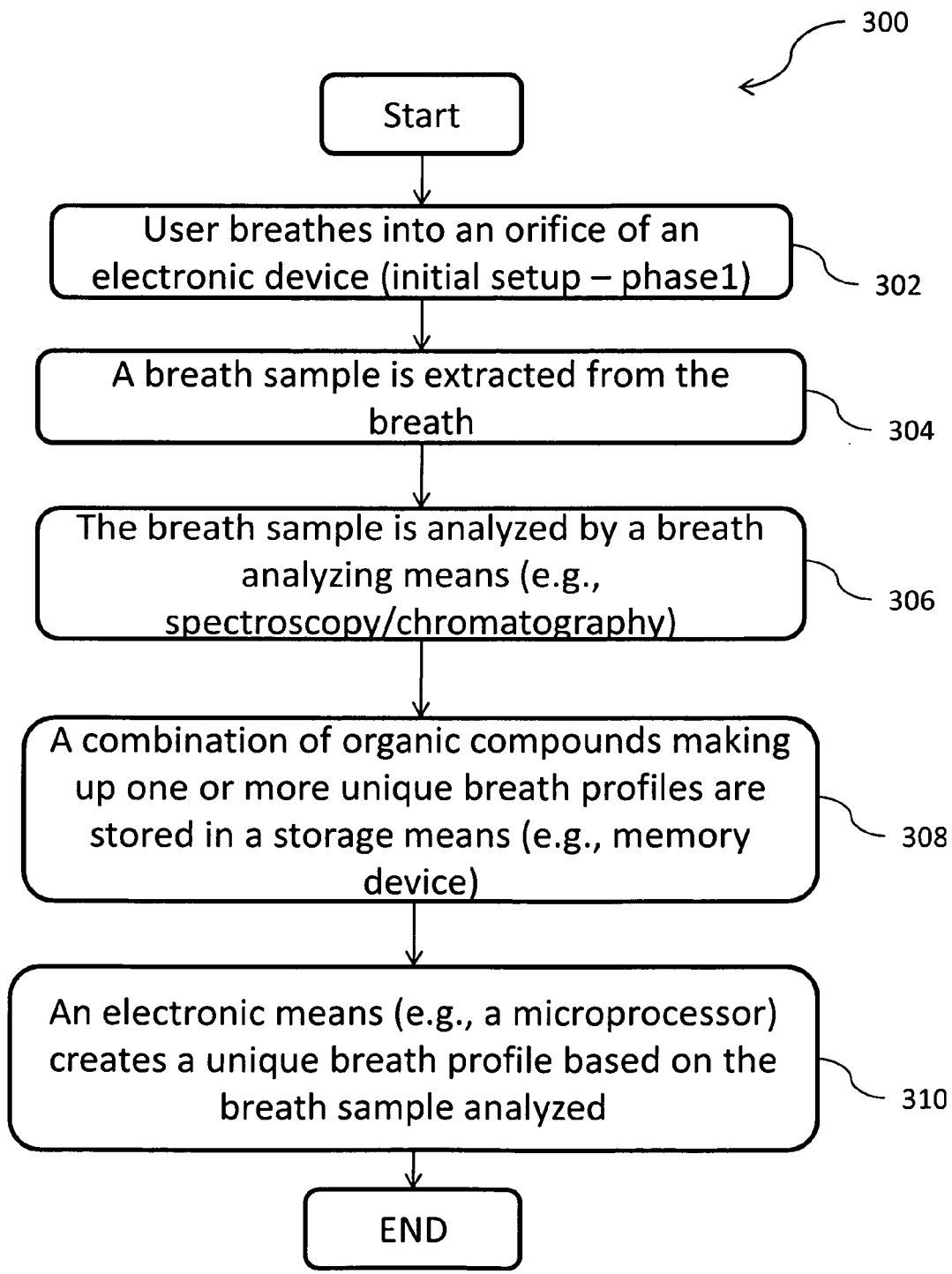
FIG. 3 is a flowchart illustrating an initial setup of inputting breath samples to create an initial breath profile to be stored in a storage unit, in accordance with the present disclosure.

With reference to FIG. 3, there is presented a flowchart illustrating an initial setup of inputting breath samples to create an initial breath profile to be stored in a storage unit, in accordance with the present disclosure.

The initial setup flowchart 300 includes the following steps. In step 302, a user breathes into an orifice or inlet or opening of the electronic device. This is the initial setup or "phase one" of the process. In step 304, a breath sample is extracted from the breath. In step 306, the breath sample is analyzed by a breath analyzing means 230 (e.g., spectroscopy and/or chromatography). In step 308, a combination of organic compounds/molecules making up one or more unique breath profiles are stored in a storage unit 236 (e.g., memory device). In step 310, an electronic means (e.g., a microprocessor) creates a unique breath profile based on the breath sampled analyzed. The initialization process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

Accordingly, blocks of the flowcharts support combinations of structures for performing the specified functions and combinations of steps for performing the specified functions. It will also be understood that each block of the flowcharts, and combinations of blocks in the flowcharts, may be implemented by special purpose hardware-based computer systems, which perform the specified functions or steps, or combinations of special purpose hardware and computer instructions.

Figure 4:
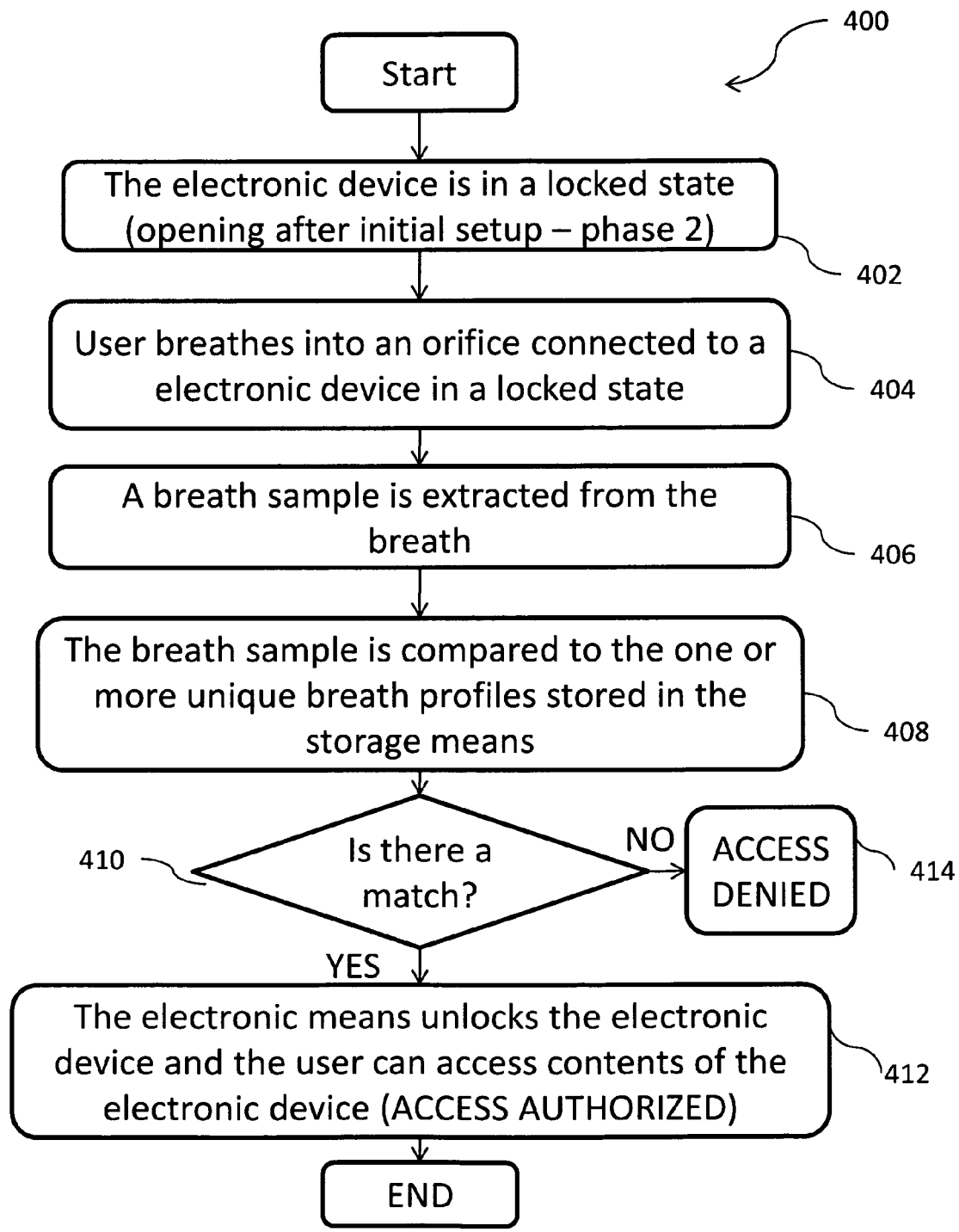
FIG. 4 is a flowchart illustrating accessing the contents of an electronic device after subsequent breath samples have been matched with the initial breath samples, in accordance with the present disclosure.

With reference to FIG. 4, there is presented a flowchart illustrating accessing the contents of an electronic device after subsequent breath samples have been matched with the initial breath samples, in accordance with the present disclosure.

The authorization/access flowchart 400 includes the following steps. In step 402, the electronic device may be in a locked state. This is the "second phase" or opening after initial setup, also referred to as "access/authorization phase." In step 404, the user breathes into an orifice or inlet or opening attached to or embedded within or incorporated within the electronic device, as defined herein. In step 406, a breath sample is extracted from the subsequent or second breath. In step 408, the breath sample is compared to the one or more unique breath profiles stored in the storage unit during the initialization phase (see FIG. 3). In step 410, a decision is made whether there is a match between the initial breath profile and the recently inputted or subsequent breath sample. If there is no match, then the process flows to step 414 where access is denied. This simply means that the subsequent user is not permitted to use or access the contents of the electronic device. If there is a match, the process flows to step 412, where the electronic means unlocks the electronic device and the user may access contents of the electronic device (access is authorized). This simply means that the subsequent user is attempting to access the operations of the electronic device and is permitted to do so because a match has been confirmed. The authorization process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

Accordingly, blocks of the flowcharts support combinations of structures for performing the specified functions and combinations of steps for performing the specified functions. It will also be understood that each block of the flowcharts, and combinations of blocks in the flowcharts, may be implemented by special purpose hardware-based computer systems, which perform the specified functions or steps, or combinations of special purpose hardware and computer instructions.

Figure 5:
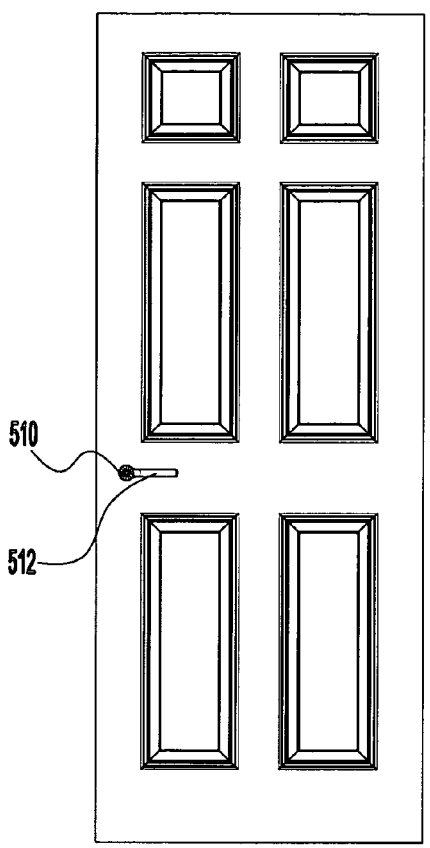
FIG. 5 is a perspective view of a door including a breath analysis module and a breath authorization module for locking/unlocking the door, in accordance with the present disclosure.

With reference to FIG. 5, there is presented a perspective view of a door including a breath analysis module and a breath authorization module for locking/unlocking the door, in accordance with the present disclosure.

The door 500 includes a handle 512 and a breath analysis system 510. The breath analysis system 510 may be embedded within the door 500 or may be attachable to the door 500. One skilled in the art may contemplate using a plurality of different means to attach/embed/incorporate the breath analysis system 510 to the door 500. Thus, the breath analysis system 510 (as described above with reference to FIGS. 1-4), may enable a user to lock/unlock the door 500 and prevent unauthorized users from entering. Therefore, breath may be used as an actuation means or authorization means to a non-electronic device, such as a door. Of course, it is contemplated that the door 500 may include other electronic components.

Figure 6:
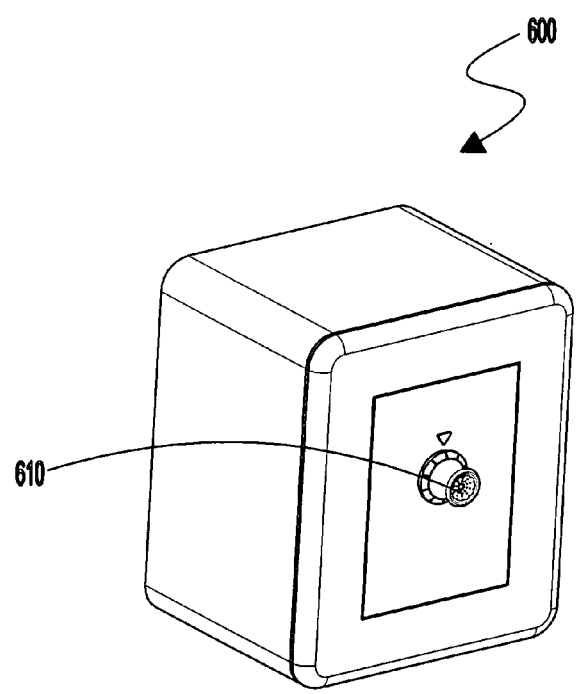
FIG. 6 is a perspective view of a safe including a breath analysis module and a breath authorization module for locking/unlocking the safe, in accordance with the present disclosure.

With reference to FIG. 6, there is presented a perspective view of a safe including a breath analysis module and a breath authorization module for locking/unlocking the safe, in accordance with the present disclosure.

The safe 600 includes a breath analysis system 610. The breath analysis system 610 may be embedded within the safe 600 or may be attachable to the safe 600. One skilled in the art may contemplate using a plurality of different means to attach/embed/incorporate the breath analysis system 610 to the safe 600. Thus, the breath analysis system 610 (as described above with reference to FIGS. 1-4), may enable a user to lock/unlock the safe 600 and prevent unauthorized users from accessing the contents of the safe. Therefore, breath may be used as an actuation means or authorization means to a non-electronic device, such as a safe. Of course, it is contemplated that the safe 600 may include other electronic components.

Figure 7:
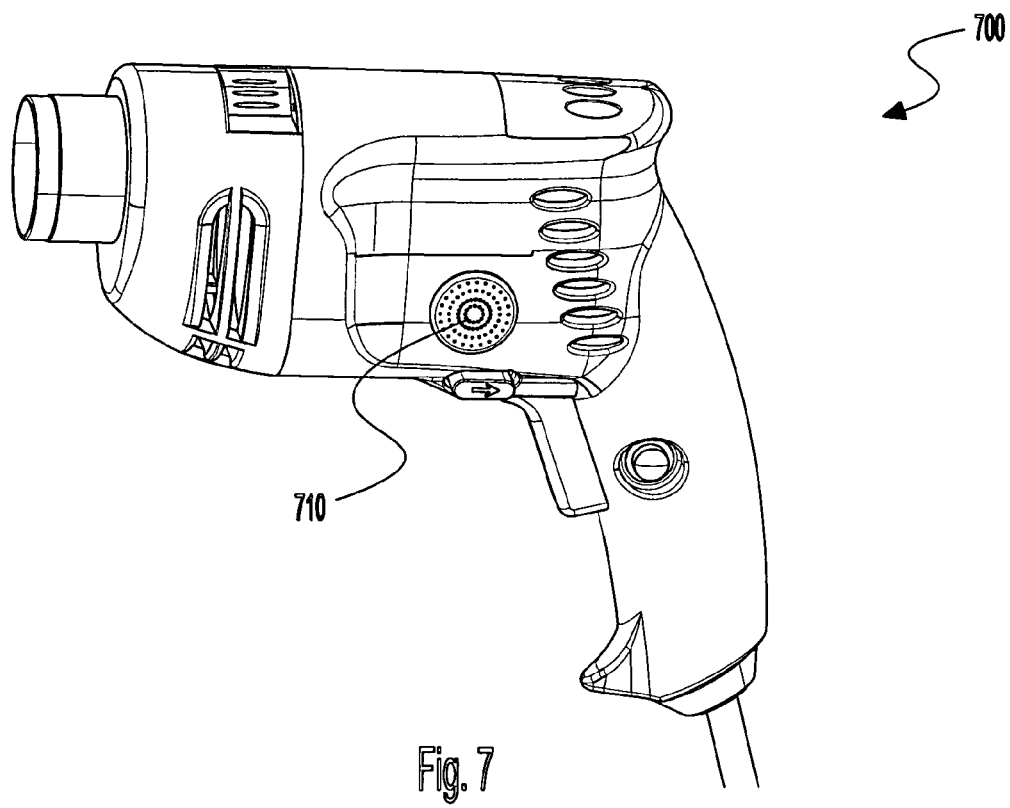
FIG. 7 is a perspective view of a power screwdriver including a breath analysis module and a breath authorization module for allowing or preventing access to the power screwdriver, in accordance with the present disclosure.

With reference to FIG. 7, there is presented a perspective view of a power screwdriver including a breath analysis module and a breath authorization module for allowing or preventing access to the power screwdriver, in accordance with the present disclosure.

The power screwdriver 700 includes a breath analysis system 710. The breath analysis system 710 may be embedded within the power screwdriver 700 or may be attachable to the power screwdriver 700. One skilled in the art may contemplate using a plurality of different means to attach/embed/incorporate the breath analysis system 710 to the power screwdriver 700. Thus, the breath analysis system 710 (as described above with reference to FIGS. 1-4), may enable a user to lock/unlock the power screwdriver 700 and prevent unauthorized users from using a potentially dangerous tool. Therefore, breath may be used as an actuation means or authorization means to a non-electronic device, such as a power screwdriver. Of course, it is contemplated that the power screwdriver 700 may include other electronic components. Thus, for example, such breath access prevention means may be used to prevent children or teens in a household from using such power tools without permission from their parents.

Figure 8:
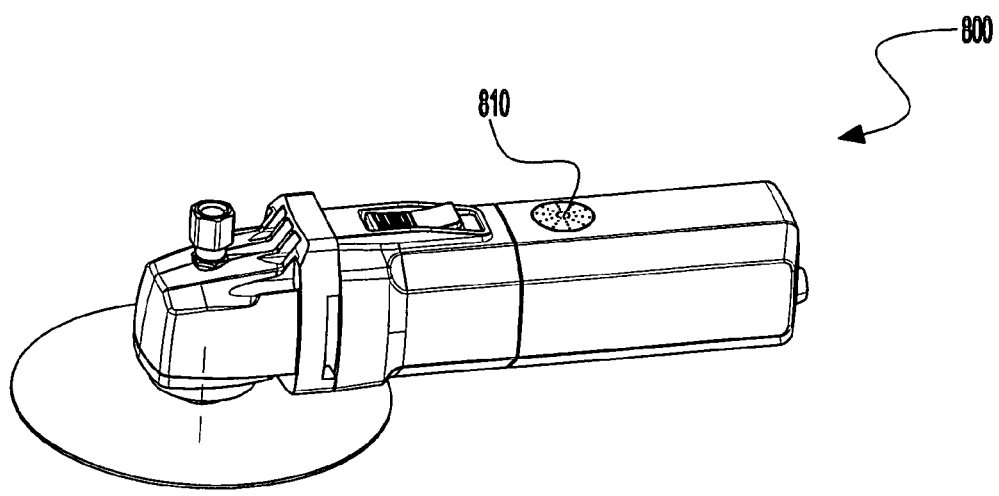
FIG. 8 is a perspective view of a circular saw including a breath analysis module and a breath authorization module for allowing or preventing access to the circular saw, in accordance with the present disclosure.

With reference to FIG. 8, there is presented a perspective view of a circular saw including a breath analysis module and a breath authorization module for allowing or preventing access to the circular saw, in accordance with the present disclosure.

The circular saw 800 includes a breath analysis system 810. The breath analysis system 810 may be embedded within the circular saw 800 or may be attachable to the circular saw 800. One skilled in the art may contemplate using a plurality of different means to attach/embed/incorporate the breath analysis system 810 to the circular saw 800. Thus, the breath analysis system 810 (as described above with reference to FIGS. 1-4), may enable a user to lock/unlock the circular saw 800 and prevent unauthorized users from using a potentially dangerous tool. Therefore, breath may be used as an actuation means or authorization means to a non-electronic device, such as a circular saw. Of course, it is contemplated that the circular saw 800 may include other electronic components. Thus, for example, such breath access prevention means may be used to prevent children or teens in a household from using such power tools without permission from their parents.

Figure 9:
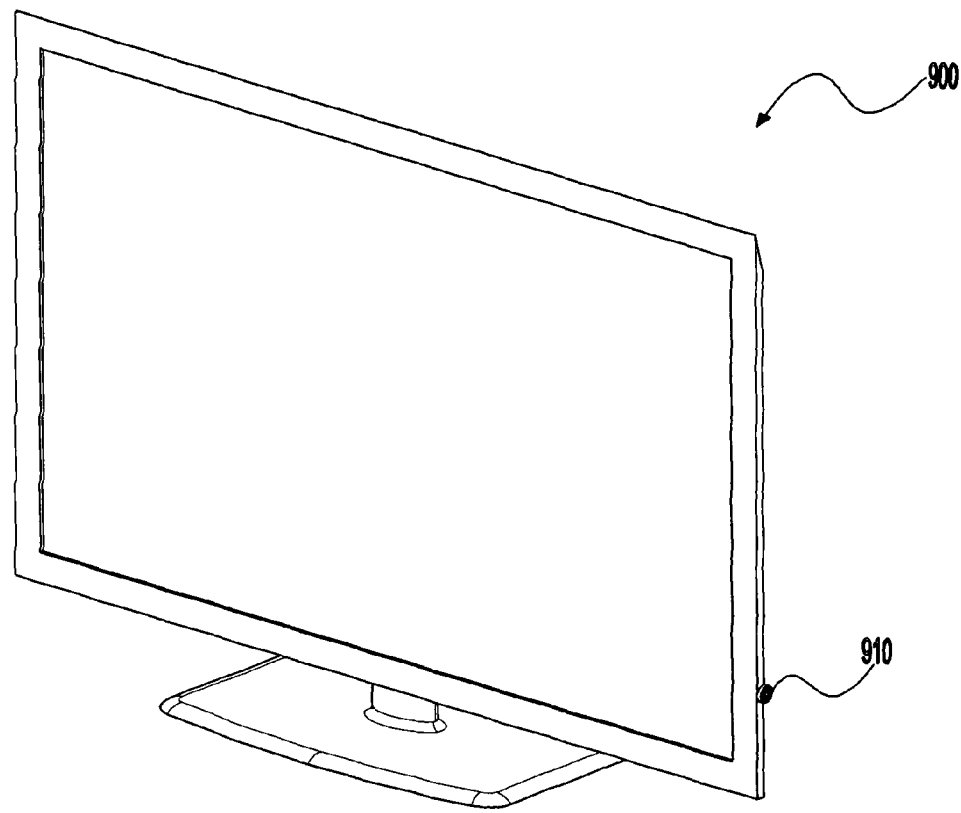
FIG. 9 is a perspective view of a television including a breath analysis module and a breath authorization module for allowing or preventing access to the television, in accordance with the present disclosure.

With reference to FIG. 9, there is presented a perspective view of a television including a breath analysis module and a breath authorization module for allowing or preventing access to the television, in accordance with the present disclosure.

The television 900 includes a breath analysis system 910. The breath analysis system 910 may be embedded within the television 900 or may be attachable to the television 900. One skilled in the art may contemplate using a plurality of different means to attach/embed/incorporate the breath analysis system 910 to the television 900. Thus, the breath analysis system 910 (as described above with reference to FIGS. 1-4), may enable a user to lock/unlock the television 900 and prevent unauthorized users from using accessing the contents/operations/applications of the television 900. Therefore, breath may be used as an actuation means or authorization means to an electronic device, such as a television. Thus, for example, such breath access prevention means may be used to prevent children or teens in a household from watching television or watching movies streamed through the television or downloading movies. Moreover, such breath access prevention means may be used to prevent, for example, contractors or painters or carpenters or other professional individuals who access a house to perform work duties, from accessing the television (or other electronics or non-electronic devices) and preventing the viewing of movies or the use of a door to a particular room or the access to safe, etc. Additionally, in another example, a gaming system may be deactivated until the children complete their homework. As such, the breath analysis system may be incorporated on the TV or directly onto the gaming system (e.g., PlayStation®, Wii®, Xbox®, etc.). One skilled in the art may contemplate a plurality of different uses for such breath actuation/prevention mechanism described with respect to the exemplary embodiments of the present disclosure.

Figure 10:
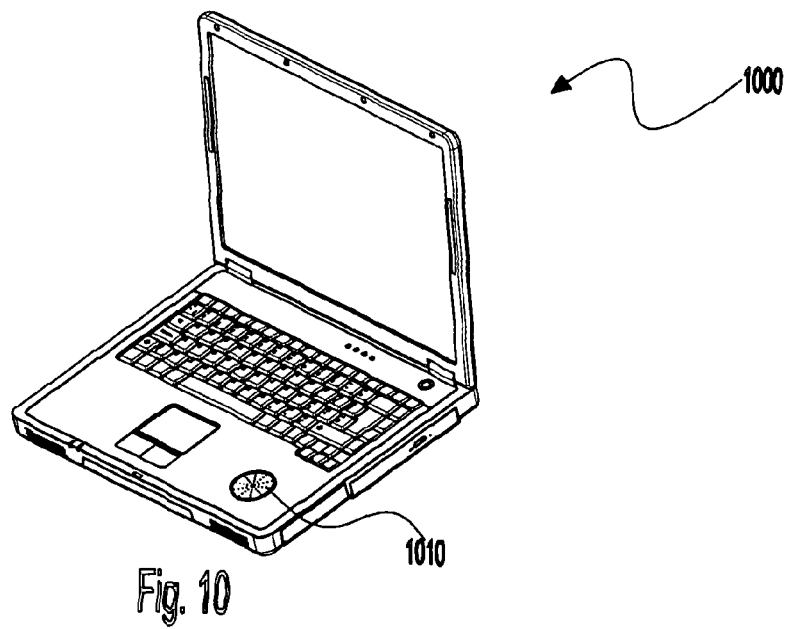
FIG. 10 is a perspective view of a laptop computer including a breath analysis module and a breath authorization module for allowing or preventing access to the laptop computer, in accordance with the present disclosure.

With reference to FIG. 10, there is presented a perspective view of a laptop computer including a breath analysis module and a breath authorization module for allowing or preventing access to the laptop computer, in accordance with the present disclosure.

The laptop computer 1000 includes a breath analysis system 1010. The breath analysis system 1010 may be embedded within the laptop computer 1000 or may be attachable to the laptop computer 1000. One skilled in the art may contemplate using a plurality of different means to attach/embed/incorporate the breath analysis system 1010 to the laptop computer 1000. Thus, the breath analysis system 1010 (as described above with reference to FIGS. 1-4), may enable a user to lock/unlock the laptop computer 1000 and prevent unauthorized users from using accessing the contents/operations/applications of the laptop computer 1000. Therefore, breath may be used as an actuation means or authorization means to an electronic device, such as a laptop computer. Additionally, for example, such breath access prevention means may be used to prevent children or teens in a household from browsing through files or watching movies streamed through the laptop computer or downloading movies/music, etc. One skilled in the art may contemplate a plurality of different uses for such breath actuation/prevention mechanism described with respect to the exemplary embodiments of the present disclosure.

Figure 11A:
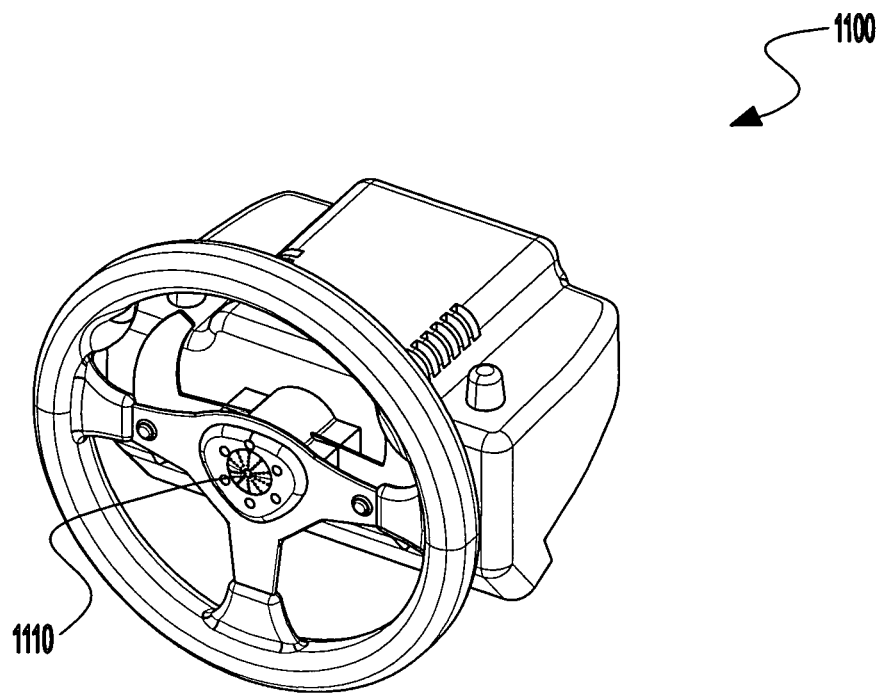
FIG. 11A is a perspective view of a steering wheel including a breath analysis module and a breath authorization module for allowing or preventing access to operating the vehicle, in accordance with the present disclosure.

With reference to FIG. 11A, there is presented a perspective view of a steering wheel including a breath analysis module and a breath authorization module for allowing or preventing access to operating a vehicle, in accordance with the present disclosure.

The steering wheel 1100 includes a breath analysis system 1110. The breath analysis system 1110 may be embedded within the steering wheel 1100 or may be attachable to the steering wheel 1100. One skilled in the art may contemplate using a plurality of different means to attach/embed/incorporate the breath analysis system 1110 to the steering wheel 1100. Thus, the breath analysis system 1110 (as described above with reference to FIGS. 1-4), may enable a user to lock/unlock the steering wheel 1100 and prevent unauthorized users from accessing the vehicle. Therefore, breath may be used as an actuation means or authorization means to a non-electronic device, such as a steering wheel. Of course, it is contemplated that the steering wheel 1100 may include other electronic components. Therefore, for example, the steering wheel may be used to prevent unauthorized individuals from driving the vehicle, such as teens in the household or potential car thieves.

Figure 11B:
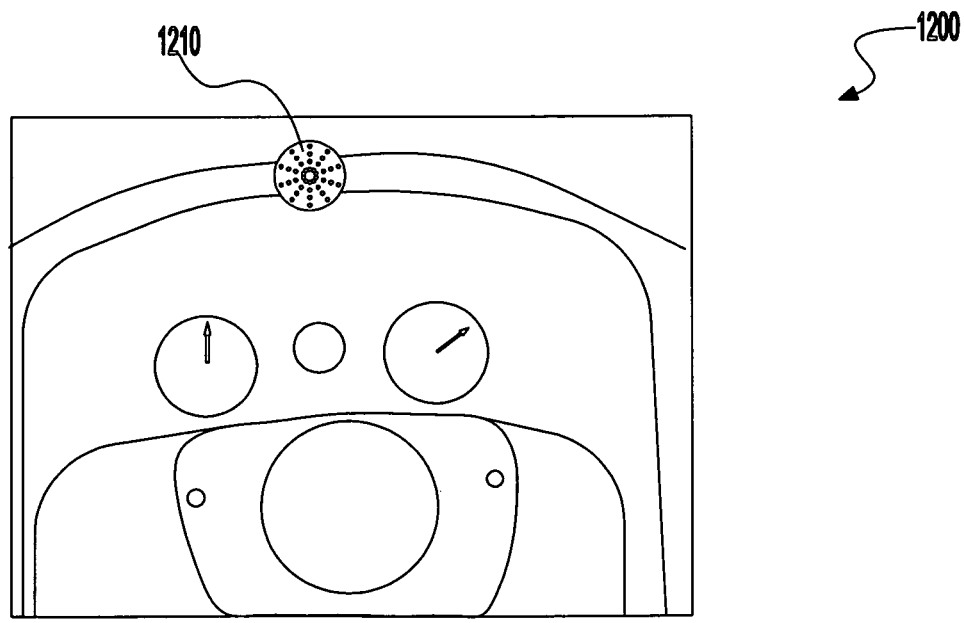
FIG. 11B is a perspective view of an interior portion of a vehicle including a breath analysis module and a breath authorization module for allowing or preventing access to operating the vehicle, in accordance with the present disclosure.

With reference to FIG. 11B, there is presented a perspective view of an interior portion of a vehicle including a breath analysis module and a breath authorization module for allowing or preventing access to operating the vehicle, in accordance with the present disclosure.

The dashboard 1200 includes a breath analysis system 1210. The breath analysis system 1210 may be embedded within the dashboard 1200 or may be attachable to the dashboard 1200. One skilled in the art may contemplate using a plurality of different means to attach/embed/incorporate the breath analysis system 1210 to the dashboard 1200. Thus, the breath analysis system 1210 (as described above with reference to FIGS. 1-4), may enable a user to lock/unlock the dashboard 1200 and prevent unauthorized users from accessing the vehicle. Therefore, breath may be used as an actuation means or authorization means to a non-electronic device, such as dashboards in a vehicle.

Of course, one skilled in the art may contemplate incorporating a breath actuation/prevention system on any portion, interior or exterior, of a vehicle. For example, instead of using the traditional keys to open a vehicle and start a vehicle, a first breath actuation/prevention system may be positioned on an exterior door or window of a vehicle to enter the vehicle and a second breath actuation/prevention system may be positioned on the steering wheel or dashboard or any other interior portion of the vehicle to start the vehicle. It is contemplated that a plurality of breath actuation/prevention systems may be incorporated in several different portions of a vehicle to access several different functions (e.g., a radio, an MP3 player, a television embedded in the back seats, opening/closing windows, etc.).

It is noted that all the electronic and non-electronic devices of FIGS. 5-11B may include indication/notification units or mechanisms as described above with reference to FIG. 1. These may be separate and distinct indication/notification units or mechanisms. However, it is contemplated that the indication/notification units or mechanisms are in electrical communication with user interfaces of the electronic and non-electronic devices. The user interfaces may display messages in text format to indicate access authorization or prevention of access.

Therefore, in summary, analysis of breath samples for non-diagnostic purposes has the advantage that the breath sample to be analyzed is collected from the user in a non-invasive manner with a minimum of discomfort or inconvenience. Since breath is the only biological fluid that may be obtained noninvasively and on demand, it is currently the matrix of choice for a number of applications. As a result, since the human body includes chemical compounds, and such chemical compounds are found in the breath of a person, such breath may be analyzed to create unique breath profiles and either allow access or deny access to electronic or non-electronic devices in a multitude of applications.

Optionally, more than one orifice, or inlet, or opening or breath receiving means may be used. For example, two breath receiving means may be used on the same electronic or non-electronic device. One breath receiving means may pertain to a first person and one breath receiving means may pertain to a second person. One person may be the husband and the other person may be the wife who is sharing the same type of device. Again, one person may be a parent using one function of the device and the other person may be a teenager using a different type function of the same device. One person may be a parent who may access a cell phone for every function available and one person may be a teenager that is authorized to access the cell phone only for calling (e.g., not for texting or playing video games or downloading apps). The possibilities are limitless.

Therefore, the breath actuation/prevention systems described herein permit a plurality of different breaths to allow or prevent access to a select number of functions/operations/applications of an electronic device. One breath may actuate 2-3 functions, whereas a second breath may actuate 2-3 other functions of the same electronic device. It is contemplated that some overlap may exist between functions permitted to be accessed. All the electronic devices may be provided with software to display a user interface to allow a user to interact with the electronic device to select which functions should and may be accessed by which individuals. Thus, a first breath input may permit access to a first set of operations and a second breath input may permit access to a second set of operations, the second set of operations being different than the first set of operations (or including some overlap between the functions).

Optionally, there may be one orifice or opening or inlet or breath receiving means that accepts more than one unique profile. In other words, 2 or 3 breath profiles of 2 or 3 different individuals may be programmed into the memory or storage unit. All the users may use the same orifice or separate orifices may be provided for each user breath profile. Of course, each orifice may trigger a different breath profile or in the alternative different breath profiles may be triggered by using the same orifice, as long as the memory device has the different breath profiles stored and identified to specific users.

Optionally, any type of timing requirements may be programmed and saved into the electronic and non-electronic devices of the exemplary embodiments of the present disclosure. For example, a sound emitting mechanism (or other type of notifying mechanism, e.g., text or color) may emit a sound to indicate that a reading should take place, for instance, every 2 hours, every 4 hours, every day in the morning and evening, etc. The timing requirements may be automated or may be programmed by the parents. For instance, the breath analysis module may require the user to reset his/her breath profile every month or every 3 months to maintain updated unique breath profiles, as such breath profiles may change upon the passage of time.

Optionally, data from a particular user may be stored so that multiple samples over an extended period of time may be taken. This permits a baseline to be established for a particular user, and trend analysis may be performed on the resulting data, relative to the database of breath profiles. If there is an acute and significant change in the chronic condition of the user's breath, indications of this change may be communicated to a physician or healthcare provider or to the parent of the user. In other words, this is a dynamic system that allows for updated/revised breath profiles to be stored based on a user's changed health circumstances. Therefore, in addition to allowing or preventing access to electronic and non-electronic devices, the breath analysis system may collect data on a person's health and convey such data to a user or to a health care professional, by for example, wireless means.

Optionally, the breath analysis information stored in the electronic and non-electronic devices may be wirelessly transferred to another electronic device or to an external database. Additionally, since a user may have several electronic devices, the breath analysis data (initial breaths and subsequent breaths) may be readily transmitted between electronic and non-electronic devices.

Optionally, in the exemplary embodiments, the breath profile may be loaded directly into each electronic or non-electronic device. However, the breath profile may be loaded by a user from an external location or from a central location. Such central location could be a single central breath receiving device for receiving breath samples to compute unique breath profiles. Once the breath profile is loaded in the single central breath receiving device, such breath profile may be transferred or transmitted (e.g., by wireless means) to the memory device of a plurality of different electronic and non-electronic devices (positioned within a predetermined or predefined radius). For example, one unique breath profile may be created and then transmitted to all the electronic devices within a single household. As such, the user need not go through an initialization process for each electronic device, but may initialize one main unit and transmit such unique breath profile to all other electronic devices within a household or a specified area (e.g., within a predetermined radius).

Optionally, the electronic and non-electronic devices may include a reset button that allows the user to reset the user's breath profile in certain circumstances.

Optionally, the results obtained from quantitative or qualitative analyses, the minimum detection analyses, and the minimum/maximum range analyses may be stored in a memory device and examined. Depending on the desired information, a computing means, such as a microprocessor, may check for significant changes in the quantitative or qualitative analyses for selected components, over time for a particular user as compared to previous breath profiles. In other words, this is a dynamic system that allows the user to constantly provide updated breath profiles and the system to adjust/modify/reconfigure the settings to provide for the most accurate, exact, concrete, distinct or definite variables and variable concentrations for creating a reliable breath match.

Optionally, an override function may be presented for overriding the breath actuation/prevention mechanism of the exemplary embodiments of the present disclosure. For example, a parent may want his child to have access to his parents' cell phone on a specific weekend. As such, the parent may temporarily override the breath accessing/prevention system for a specified period of time (e.g., a 24-hour period, a 48-hour period, a 2-hour period, etc.). For example, a household may have guests for a weekend and may wish to allow access to a specific television for the guests. As such, the head of the household may temporarily override the breath accessing/prevention system attached or connected to a television for a specified period of time. One skilled in the art may contemplate a plurality of different scenarios for using an override function. The exemplary embodiments of the present disclosure are not limited to any type of override function.

Optionally, the breath analysis may not necessarily take place before any operations or functions are provided. In other words, for certain electronic devices, the breath analysis may kick in after a period of time has passed. For example, a person may pick up another person's cell phone and start dialing a number. Once the phone starts to ring and the user places their mouth in close proximity to or in the vicinity of the breath receiving unit, a breath analysis may automatically take place and lock the cell phone. In other words, a prompt for a breath sample is not always necessary in accordance with the exemplary embodiments of the present disclosure. Instead of a prompt, the breath analysis system may automatically kick in or be activated when an attempt to commence an operation or function takes place. A predetermined period of time may pass before the breath analysis system automatically kicks in (e.g., the time it takes to determine a user is attempting an operation, a functionality, or using an app).

Within this written description, the particular naming of the components, capitalization of terms, the attributes, data structures, or any other programming or structural aspect is not mandatory or significant, and the mechanisms that implement the present disclosure or its features may have different names, formats, or protocols. Further, the breath analysis assembly may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

It should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

Having described the present disclosure above, various modifications of the techniques, procedures, material and equipment will be apparent to those in the art. It is intended that all such variations within the scope and spirit of the appended claims be embraced thereby.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

What is claimed is:

1. A mobile device comprising:
a processing unit for executing a plurality of operations;
an input module for receiving a plurality of breath samples from a plurality of users;
a breath analysis module integrated within the mobile device for chemically analyzing the plurality of breath samples of each of the plurality of users to create and associate an initial unique chemical breath profile to each of the plurality of users, each of the initial unique chemical breath profiles stored in the mobile device for comparison with subsequent chemical breath profiles, the chemical analysis involving at least identification of a plurality of uncommon molecules and uncommon organic compounds from each user for deriving distinguishing breath characteristics of each user of the plurality of users and using such breath information to create the initial chemical breath profile associated with each user of the plurality of users; and
a breath authorization module for allowing or preventing access to the plurality of operations of the mobile device in response to a comparison result derived from comparing at least one of the subsequent chemical breath profiles with each of the initial unique chemical breath profiles stored in the mobile device.

2. The mobile device according to claim 1, wherein the breath analysis module includes a breath sampling module for sampling the plurality of breath samples of each of the plurality of users.

3. The mobile device according to claim 1, wherein the user of the mobile device is prompted to reset a previously entered initial unique chemical breath profile associated with the user, the resetting involving inputting a plurality of new breath samples to create a new initial unique chemical breath profile for the user.

4. The mobile device according to claim 1, wherein each initial unique chemical breath profile is different for each user of the plurality of users.

5. The mobile device according to claim 1, wherein the initial unique chemical breath profile of each of the plurality of users is monitored for deviations, and upon detection of the deviations, creating an updated unique chemical breath profile for each user exhibiting the deviations.

6. The mobile device according to claim 1, wherein the initial unique chemical breath profile of the user of the plurality of users allows access to a predetermined number of operations of the plurality of operations available on the mobile device.

7. The mobile device according to claim 1, wherein the initial unique chemical breath profile of the user of the plurality of users is shared with other mobile devices having chemical analysis capabilities controlled by the same user.

8. The mobile device according to claim 1, further comprising an output indication unit for indicating whether the initial unique chemical breath profiles allow or prevent access to the plurality of operations of the mobile device, the output indication unit being one of a visual indication or an audible indication or a combination thereof.

9. The mobile device according to claim 1, further comprising an override function for overriding the breath authorization module.

10. The mobile device according to claim 1, wherein a first initial unique chemical breath profile of a first user permits access to a first set of operations of the mobile device and a second initial unique chemical breath profile of a second user permits access to a second set of operations of the same mobile device, the second set of operations being different than the first set of operations.

11. A method of accessing a mobile device, the method comprising:
    executing a plurality of operations via a processing unit;
    receiving a plurality of breath samples from a plurality of users;
    chemically analyzing the plurality of breath samples of each of the plurality of users, via a breath analysis module integrated within the mobile device, for creating and associating an initial unique chemical breath profile to each of the plurality of users, each of the initial unique chemical breath profiles stored in the mobile device for comparison with subsequent chemical breath profiles, the chemical analysis involving at least identification of a plurality of uncommon molecules and uncommon organic compounds from each user for deriving distinguishing breath characteristics of each user of the plurality of users and using such breath information to create the initial chemical breath profile associated with each user of the plurality of users; and
    allowing or preventing access to the plurality of operations of the mobile device, via a breath authorization module, in response to a comparison result derived from comparing at least one of the subsequent chemical breath profiles with each of the initial unique chemical breath profiles stored in the mobile device.

12. The method according to claim 11, further including sampling the plurality of breath samples of each of the plurality of users, via a breath sampling module.

13. The method according to claim 11, further comprising prompting the user of the mobile device to reset a previously entered initial unique chemical breath profile associated with the user, the resetting involving inputting a plurality of new breath samples to create a new initial unique chemical breath profile for the user.

14. The method according to claim 11, wherein each initial unique chemical breath profile is different for each user of the plurality of users.

15. The method according to claim 11, further comprising monitoring the initial unique chemical breath profile of each of the plurality of users for deviations, and upon detection of the deviations, creating an updated unique chemical breath profile for each user exhibiting the deviations.

16. The method according to claim 11, wherein the initial unique chemical breath profile of the user of the plurality of users allows access to a predetermined number of operations of the plurality of operations available on the mobile device.

17. The method according to claim 11, further comprising sharing the initial unique chemical breath profile of the user of the plurality of users with other mobile devices having chemical analysis capabilities controlled by the same user.

18. The method according to claim 11, further comprising indicating whether the initial unique chemical breath profiles allow or prevent access to the plurality of operation of the mobile device, the output indication unit being one of a visual indication or audible indication or a combination thereof.

19. The method according to claim 11, further comprising overriding the breath authorization module.

20. The method according to claim 11, where a first initial unique chemical breath profile of a user permits access to a first set of operations of the mobile device and a second initial unique chemical breath profile of a second user permits access to a second set of operations of the same mobile device, the second set of operations being different than the first set of operations.

* * * * *